United States Patent [19]

Karst

[11] Patent Number: 4,950,160

[45] Date of Patent: Aug. 21, 1990

[54] INSTRUMENT FOR STAIN REMOVAL AND POLISHING OF NATURAL TEETH

[76] Inventor: L. Emery Karst, 317 San Rodee Dr. SE., Salem, Oreg. 97301

[21] Appl. No.: 128,157

[22] Filed: Dec. 3, 1987

Related U.S. Application Data

[63] Continuation-in-part of Ser. No. 886,443, Jul. 17, 1986, abandoned.

[51] Int. Cl.$^5$ .............................................. A61C 3/02
[52] U.S. Cl. .......................................... 433/88; 433/87
[58] Field of Search .................. 433/80, 88 O, 88, 125; 222/575

[56] References Cited

U.S. PATENT DOCUMENTS

| | | | |
|---|---|---|---|
| 1,699,532 | 1/1929 | Hopkins | 222/575 |
| 3,972,123 | 8/1976 | Black | 433/88 |
| 4,174,571 | 11/1979 | Gallant | 433/88 |
| 4,248,589 | 2/1981 | Lewis | 433/80 |
| 4,494,932 | 1/1985 | Rzewinski | 433/88 |
| 4,540,365 | 9/1985 | Nelson et al. | 433/88 |
| 4,648,840 | 3/1987 | Conger, Sr. | 433/125 |

FOREIGN PATENT DOCUMENTS

| | | | |
|---|---|---|---|
| 0163610 | 2/1985 | European Pat. Off. | |
| 0331042 | 8/1958 | Switzerland | 433/80 |

*Primary Examiner*—Gene Mancene
*Assistant Examiner*—Adriene B. Lepiane
*Attorney, Agent, or Firm*—Chernoff, Vilhauer, McClung & Stenzel

[57] ABSTRACT

A dental tool for polishing teeth with an abrasive-laden air stream, surrounded by a water curtain, includes a pistol-grip handle and a nozzle connected to a manifold at an obtuse angle to one another. A canister, located atop the manifold and having a detachable lid, houses abrasive powder and is connected between the air input and output lines of the manifold. A thumb-actuated plunger regulates the amount of air entering the canister, and thus controls the volume of the abrasive-laden air stream exiting the nozzle. The nozzle includes a pinched orifice for the abrasive-laden air stream so that it fans out across the surface of the tooth to be cleaned.

9 Claims, 2 Drawing Sheets

INSTRUMENT FOR STAIN REMOVAL AND POLISHING OF NATURAL TEETH

RELATED APPLICATIONS

This application is a continuation-in-part of Patent application Ser. No. 886,443 filed July 17, 1986, now abandoned.

FIELD OF THE INVENTION

The present invention relates to a hand-held dental tool for the polishing of natural teeth using an abrasive-laden air stream and water.

BACKGROUND OF THE INVENTION

A significant problem in the field of dentistry has been to remove stain from the surface of a patient's teeth even after a thorough prophylaxis (cleaning) has been completed. Many different types of devices have been proposed for this type of stain removal. One class of such devices includes a hand held tool having inputs for air and water under pressure and a spray nozzle for directing the air and water mixture at the tooth. Such tools usually also include a box or chamber for mixing an abrasive powder with the air so that the nozzle produces a spray consisting of an abrasive-laden air stream mixed with water, as shown, for example, in Nelson et al. U.S. Pat. No. 4,540,365. The Nelson tool includes a mixing chamber in the handle in which air agitates particulate matter in the chamber causing it to flow as an abrasive-laden stream towards an orifice. The Nelson device, however, includes a mixing chamber which is interior to the handle. It is thus awkward and difficult to load the abrasive material into the mixing chamber. Also, with the Nelson device, water and an abrasive-laden air stream are mixed prior to the exit from the nozzle. This is undesirable because a wet slurry is formed inside the nozzle which may clog the entrance and which is less precisely directed by the nozzle.

A similar device is shown in the U.S. Pat. to Conger, No. 4,648,840 which includes a pencil-like handle which includes a downwardly-extending canister for holding an abrasive powder, and a nozzle having an interior conduit for carrying an abrasive-laden air stream surrounded by a conduit for carrying water. The two streams are mixed at the forward end of the conduits. The Conger device is more easily loaded with abrasive powder than is the Nelson device, because the downwardly-extending canister may be unscrewed from the handle. The way in which the Conger device is held, however, makes it awkward to use. The handle of the Conger device is adapted to be grasped like a pencil but the downwardly-extending canister can make its use inconvenient. Also, the body of the Conger device is too large for it to be easily grasped in this manner. A similar device is shown in European Patent Application No. 0,163,610 published Apr. 12, 1985.

In yet another patent, Black, U.S. Pat. No. 3,972,123, a nozzle is shown which includes an outlet for an air/abrasive mixture and water outlets surrounding the air/abrasive outlet tilted toward the abrasive outlet so that the water streams converge on the abrasive-laden air stream. This system, however, is undesirable because such an arrangement creates a pinpoint stream which concentrates both streams at a particular point on the tooth and does not fan out over the surface of the tooth.

What is needed therefore is a dental cleaning tool of the type utilizing an air/abrasive stream surrounded by a water curtain that may be easily grasped and controlled, and having a nozzle which ensures that the air/abrasive-water mixture will fan out across the area to be cleaned.

SUMMARY OF THE INVENTION

The present invention meets the abovementioned needs. The invention herein comprises an inverted Y-shaped tool wherein one of the legs of the "Y" comprises a pistol-grip handle and the other comprises an outlet nozzle for providing a spray which includes an air abrasive mixture surrounded by a water curtain. The upwardly-extending leg of the "Y" includes a mixing chamber having a selectively detachable top into which an abrasive powder may be loaded. The handle, the nozzle and the mixing chamber are connected to a manifold containing air and water input and output lines, respectively, and a thumb-actuated valve through which the flow of air into the mixing chamber is controlled. The mixing chamber includes an input aperture at its bottom and an upright output tube extending from the bottom of the chamber to a point just below the top, so that air entering from below creates an abrasive-laden air stream which is forced downwardly into the output tube, through the manifold to the nozzle. When the handle is grasped in pistol-like fashion, the thumb-actuated switch is easily controlled to provide proportional control of the amount of air entering the mixing chamber and, hence, exiting from the nozzle.

The nozzle includes an outer water conduit and an inner conduit for the abrasive-laden air stream. The outer conduit terminates in a series of apertures which provide a water curtain surrounding the inner conduit. The inner conduit extends past the apertures in the outer conduit and includes an aperture comprising two partially circular orifices which are formed by a partial crimp in the end of the inner conduit. This crimp causes the abrasive laden air stream to fan out from its orifice so that a broader area of application is created.

The dental tool of the present invention is therefore easier to grasp, manipulate and use than those shown in the prior art. It is also easier to load and unload the abrasive powder and provides a spray which fans out across the surface of the tooth to be polished without clogging any of the orifices at the end of the nozzle.

It is a primary object of this invention to provide a dental tool for removing stains which is effective and easy to use.

Yet a further object of this invention is to provide a dental tool utilizing an abrasive-laden air spray which includes a mixing canister conveniently located on the tool which may be loaded by merely removing the top of the canister.

Yet a further object of this invention is to provide a dental tool utilizing an abrasive laden air stream surrounded by a water curtain which provides the right mixture of air, abrasive and water over a wide area to be cleaned.

The foregoing and other objectives, features and advantages of the present invention will be more readily understood upon consideration of the following detailed description of the invention taken in conjunction with the accompanying drawings.

DETAILED DESCRIPTION OF THE INVENTION

Figure 1:
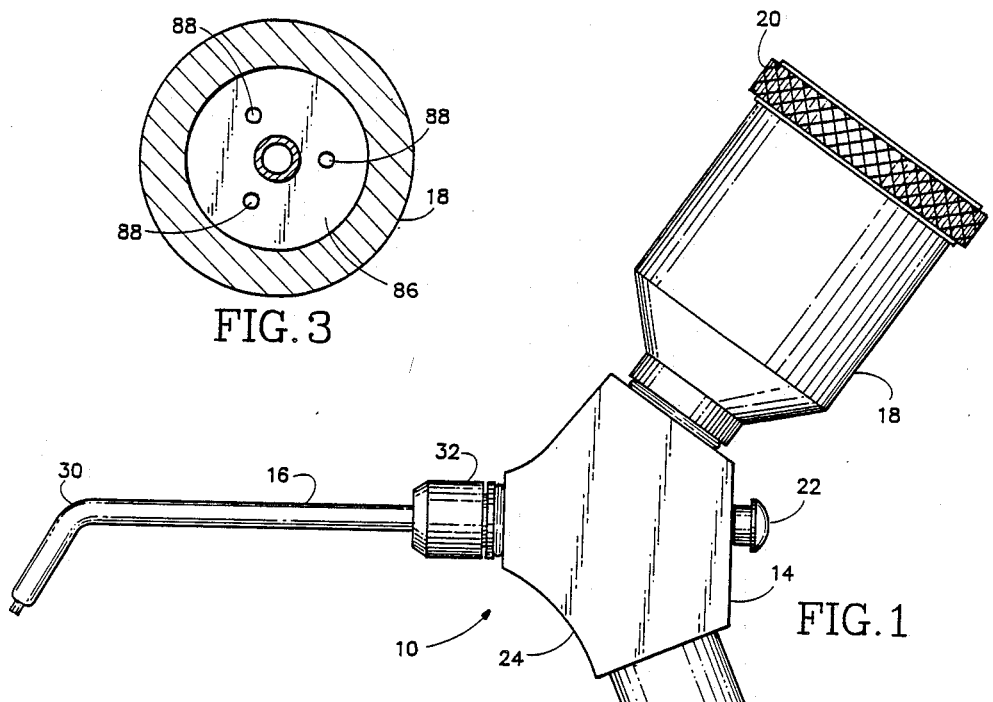
FIG. 1 is a side view of a dental tool comprising the present invention.

Referring now to FIG. 1, a dental tool 10 comprises a handle 12, which is adapted to be gripped in pistol-like fashion, which is affixed to a manifold 14. The tool 10 resembles an inverted Y-shape when properly grasped and has a nozzle 16 forming one of the legs of the Y with the handle 12 forming the other. The nozzle 16 and the handle 12 extend at an obtuse angle with respect to one another of less than 180°. The upright leg of the inverted Y is represented by a mixing chamber 18. Mixing chamber 18 has a selectively removable threaded lid 20. The manifold 14 includes a thumb-actuated plunger 22 and the underside of manifold 14 is a curved surface 24 which may be supported by the index finger when the handle 12 is gripped in pistol-like fashion. Extending through the handle 12 is a water input line 26 and an air input line 28. The nozzle 16 includes an obtuse elbow bend 30 so that the cleaning streams from the nozzle 16 may be properly directed to the teeth when the handle is gripped as intended. The nozzle 16 also includes a fitting 32 which allows the nozzle 16 to rotate on its axis. The tool 10 is adapted to be connected to any conventional dental air and water supply, the details of which are well known in the art and are not considered part of this invention.

Figure 2:
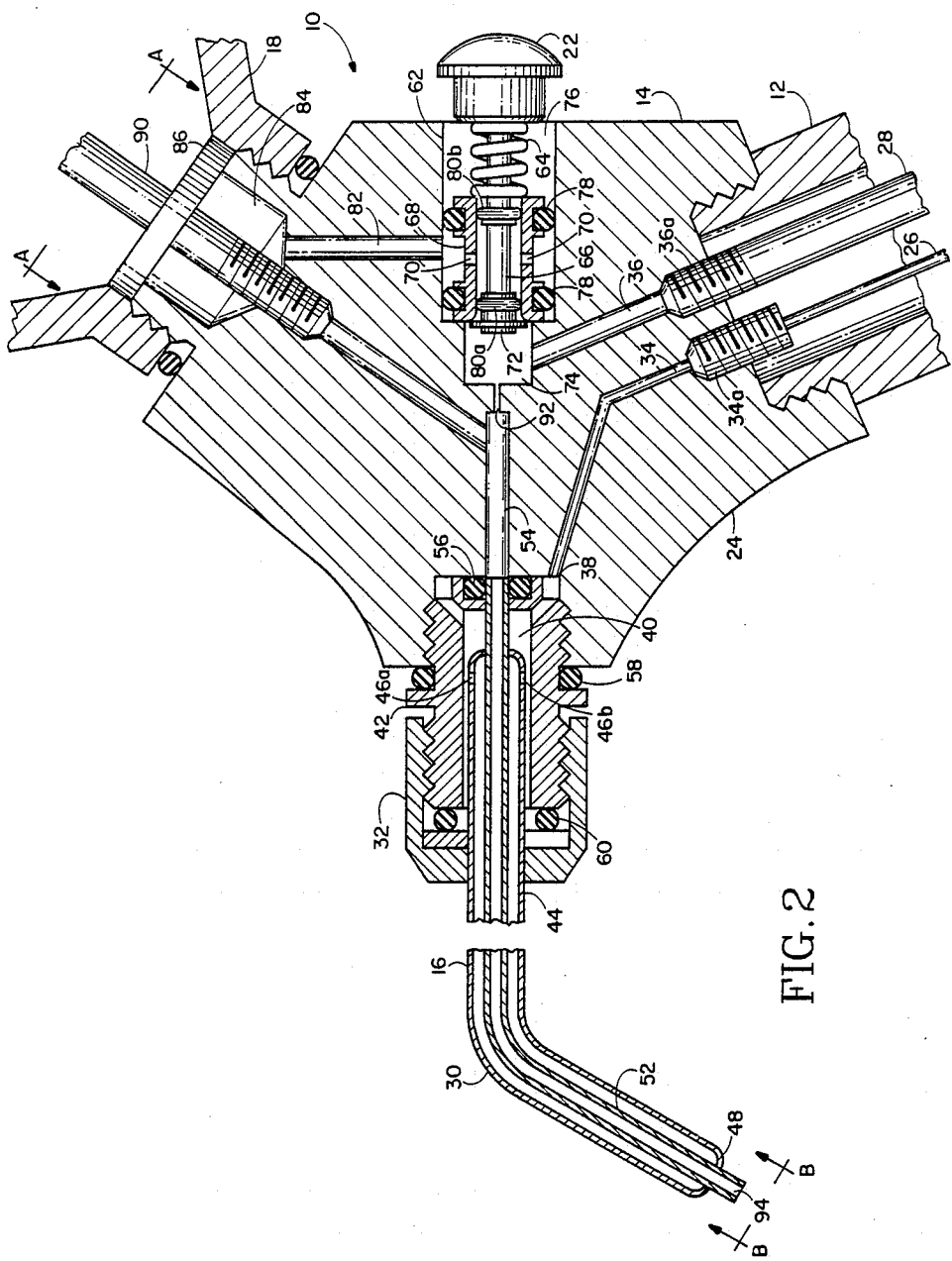
FIG. 2 is a partial cutaway side view of the dental tool of FIG. 1.

Referring now to FIG. 2, the air and water conduits 28 and 26, respectively, extend through a hollow portion of handle 12 and are coupled to air and water input lines 34 and 36, respectively, through fittings 34a and 36a. The water input line 34 extends through a bore in manifold 14 to an output point 38 where the water enters a chamber 40 in a threaded fitting 42. The hollow interior 40 of the threaded fitting 42 houses a water conduit 44 which includes a pair of apertures 46a and 46b for the water to enter. The water conduit 44 terminates in a rounded forward end 48 which includes a plurality of apertures 50 for creating a shower-like water curtain.

The water conduit 44 surrounds an interiorly disposed air conduit 52 which extends through the hollow portion 40 of the fitting 42 to an air/abrasive output line 54 on the manifold 14. The fitting 42 is threaded into the manifold 14 and is tightened against the output line 54 and sealed with an O-ring 56. A watertight seal between the fitting 42 and the manifold 14 is provided by an O-ring 58. Fitting 32 is threaded onto fitting 42 and is sealed tightly by O-ring 60. Thus, the nozzle 16 may be rotated without loosening the fitting 32 and impairing the tightness of the seal. The air input line 36 is connected to a valve assembly 62 which includes a thumb actuated plunger 22 urged in an outward direction by a spring 64. The plunger 22 includes an interior piston 66 which moves within a cylinder 68. The cylinder 68 includes apertures 70, and the piston 66 includes a cap 72 which extends into a chamber 74. The entire assembly 62 is tightly sealed inside a bore 76 by O-rings 78. O-rings 80a and 80b are disposed about the piston 66 and serve to seal off the air which is pressurized in chamber 74, keeping it from exiting the apertures 70 until the plunger is depressed far enough so that the cap 72 lifts and the O-ring 80a begins to clear the entrance to the chamber 74. When this occurs an opening appears due to the slight outward taper of cylinder 68 allowing air to flow from line 36 through chamber 74 into cylinder 68 where it may exit through apertures 70 into the interior of the bore 76 contained by O-rings 78. The air will then flow into a valve output line 82 which enters an input chamber 84 in the bottom of mixing chamber 18. The amount of air flow entering line 82 is proportionally controlled by the plunger 22 because the farther plunger 22 is depressed against the action of spring 64, the larger is the opening created in chamber 74.

Figure 3:
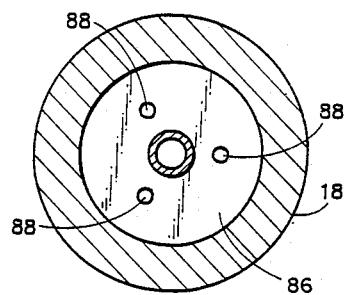
FIG. 3 is a partial cutaway view taken along line A—A of FIG. 2.

The mixing canister 18 includes a circular plate 86 at its bottom which contains three apertures 88 (refer to FIG. 3). Also extending through the plate 86 is an output tube 90 which extends upwardly through the mixing chamber 18 to a point just below the top of the detachable lid 20. The tube 90 is connected to the air output line 54 on the manifold 14.

Interposed between the air output line 54 and the interior chamber 74 is a restricted orifice 92 which may include a needle valve. The orifice 92 allows a minimum amount of air to flow into the conduit 52 at all times even when plunger 22 is fully retracted sealing off chamber 74.

Figure 4:
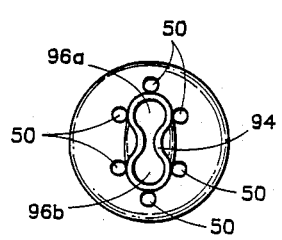
FIG. 4 is an end view taken along line B—B of FIG. 2.

When air enters the mixing chamber 18 through apertures 88, the powder which has settled in the bottom of the chamber 18 is agitated, mixed with the air, and is forced downwardly through output tube 90 to the air output line 54 on manifold 14. The air, which is now laden with the powdered abrasive, is forced out through the forward end 94 of interior conduit 52. The end 94 extends past the end of the water conduit 44 by a small amount to keep the abrasive-laden air stream separate from the water at the point of origin. In cross section (refer to FIG. 4) the tube end 94 is crimped to provide a pair of partially circular orifices 96a and 96b which are joined together. This causes the abrasive-laden air stream to fan out so that the spray covers a wide area of the tooth to be polished. Moreover, since the end 94 extends past the water conduit end 48, the abrasive-laden air stream does not form a slurry with the water curtain until both streams are adjacent the teeth. This helps to prevent clogging of the orifices on the nozzle 16.

When the handle is grasped in pistol like fashion, the index finger rests underneath surface 24 and the thumb rests on plunger 22. Gently pushing on plunger 22 thus provides a fine degree of control for the amount of abrasive-laden air desired by the dentist. Furthermore, convenience is maximized by locating the cannister or mixing chamber 18 at the top of the tool 10 so that it may be refilled by simply removing the detachable lid 20. When grasped in this fashion, the elbow bend 30 directs the nozzle 16 in the proper direction and the nozzle may be rotated to reach otherwise hard-to-get-to areas without reorienting the canister 18.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A dental tool for polishing teeth comprising:

(a) a handle adapted to be grasped in piston-like fashion;
(b) a manifold connected to the top of the handle, said manifold including an air input line, an air output line, a water input line and a water output line;
(c) a spray nozzle connected to the manifold and including air and water conduits connected to the air output line and the water output line of the manifold respectively, said spray nozzle extending from the manifold at an obtuse angle of less than 180° with respect to the handle; and
(d) a mixing chamber for mixing air under pressure with an abrasive powder to create an abrasive-laden air stream, comprising a canister affixed to the manifold, said canister extending substantially vertically upwards from an upper side of the manifold when said handle is grasped in pistol-like fashion, thereby forming an obtuse angle with respect to both the handle and the nozzle, said canister having a bottom portion proximate said manifold, said bottom portion including air input means communicating with said air input line of said manifold for permitting air to pass from said air input line into said bottom portion of said cannister, said canister further including a vertical output tube connected to said air output line of said manifold extending through said bottom portion of said canister to just below the top of said cannister, whereby air entering said cannister through said air input means agitates the abrasive powder forcing the abrasive-laden air stream down through said output tube to said manifold.

2. The dental tool of claim 1 wherein said manifold includes a valve for selectively gating said air input line into the air input aperture at the bottom of the canister.

3. The dental tool of claim 2 wherein said valve is a thumb-actuated plunger biased by a spring so as to normally cut off the flow of air through said manifold into said canister and having a predetermined stroke length for providing proportional control of said air flow as a function of the stroke of said plunger.

4. The dental tool of claim 3 wherein the manifold further includes a needle valve connected to the air input line, said valve having an output to the air output line to maintain a continuous partial flow of air to said nozzle when said valve is in an off position.

5. The dental tool of claim 1 wherein the air input line and the water input line on the manifold are connected to conduits extending through the handle.

6. The dental tool of claim 1 wherein the spray nozzle comprises a pair of concentrically arranged tubes including an outer tube connected to the water output line of the manifold and an inner tube connected to the air output line of the manifold, the inner tube extending slightly past the outer tube at its forward end and the outer tube including a plurality of holes at its forward end to create a water curtain surrounding the abrasive-laden air stream carried by the inner tube.

7. The dental tool of claim 6 wherein the spray nozzle has an obtuse elbow bend near its forward end.

8. The dental tool of claim 6 wherein said inner tube includes a crimped end thereby creating two partially circular orifices.

9. The dental tool of claim 1 wherein said nozzle is rotatably mounted to said manifold.

* * * * *